(12) United States Patent
Perollier et al.

(10) Patent No.: US 8,344,082 B2
(45) Date of Patent: Jan. 1, 2013

(54) MOLECULARLY IMPRINTED POLYMERS FOR THE RECOGNITION OF GLUTATHIONE GSH, METHODS FOR PREPARING SAME AND USES THEREOF

(75) Inventors: Celine Perollier, Rouen (FR); Sami Bayoudh, Rouen (FR)

(73) Assignee: Polyintell, Val de Reuil (FR)

( * ) Notice: Subject to any disclaimer, the term of this patent is extended or adjusted under 35 U.S.C. 154(b) by 428 days.

(21) Appl. No.: 12/681,977

(22) PCT Filed: Oct. 8, 2008

(86) PCT No.: PCT/FR2008/051815
§ 371 (c)(1),
(2), (4) Date: Apr. 30, 2010

(87) PCT Pub. No.: WO2009/056716
PCT Pub. Date: May 7, 2009

(65) Prior Publication Data
US 2010/0234565 A1    Sep. 16, 2010

(30) Foreign Application Priority Data

Oct. 10, 2007  (FR) ..................................... 07 58193

(51) Int. Cl.
| | |
|---|---|
| C07K 1/14 | (2006.01) |
| C08H 1/00 | (2006.01) |
| C08F 12/30 | (2006.01) |
| C08F 26/02 | (2006.01) |
| C08F 128/02 | (2006.01) |
| C08F 20/06 | (2006.01) |

(52) U.S. Cl. .................. 526/238.1; 530/331; 526/317.1; 526/286; 526/288; 526/289

(58) Field of Classification Search ............... 526/238.1, 526/286, 288, 289, 317.1; 530/331
See application file for complete search history.

(56) References Cited

U.S. PATENT DOCUMENTS
2005/0186651 A1  8/2005 Gan et al.

OTHER PUBLICATIONS

Yang et al., "Capacitive Biosensor for Glutathione Detection Based on Electropolymerized Molecularly Imprinted Polymer and Kinetic Investigation of the Recognition Process," Electroanalysis, 2005, pp. 969-977, vol. 17, No. 11.*
Soglia et al., "A Semiquantitative Method for the Determination of Reactive Metabolite Conjugate Levels in Vitro Utilizing Liquid Chromatography—Tandem Mass Spectrometry and Novel Quaternary Ammonium Glutathione Analogues," Chem. Res. Toxicol., vol. 19, No. 3, 2006, pp. 480-490.
Thompson et al., "Quinone Methide Formation from Para Isomers of Methylphenol (Cresol), Ethylphenol, and Isopropylphenol: Relationship to Toxicity," Chem. Res. Toxicol., vol. 8, No. No. 1, 1995, pp. 55-60.
Sharma et al., "Highly Sensitive and Selective Detection of Creatinine by Combined Use of MISPE and a Complementary MIP-Sensor," Chromatographia, vol. 65, No. 7/8, 2007, pp. 419-427.

(Continued)

Primary Examiner — William Cheung
(74) Attorney, Agent, or Firm — Oliff & Berridge, PLC

(57) ABSTRACT

The present invention relates to new molecularly imprinted polymers which are suitable for the selective recognition of glutathione GSH and/or of an analog thereof, and in particular which are of use for the treatment of media comprising in particular a mixture of glutathione GSH, and/or of an analog thereof, with GSH adducts.

15 Claims, 1 Drawing Sheet

Imprint No. 1

Imprint No. 2

OTHER PUBLICATIONS

Chianella et al., "MIP-based solid phase extraction cartridges combined with MIP-based sensors for the detection of microcystin-LR," *Biosensors & Bioelectronics*, vol. 18, 2003, pp. 119-127.

International Search Report issued in Application No. PCT/FR2008/051815; Mailed on Mar. 20, 2009 (With Translation).

Written Opinion of the International Searching Authority issued in Application No. PCT/FR2008/051815; Mailed on Mar. 20, 2009 (With Translation).

Office Action issued in corresponding European Application No. 08845161.2 dated Dec. 23, 2010.

* cited by examiner

FIGURE 1A

Imprint No. 1

FIGURE 1B

Imprint No. 2

MOLECULARLY IMPRINTED POLYMERS FOR THE RECOGNITION OF GLUTATHIONE GSH, METHODS FOR PREPARING SAME AND USES THEREOF

This application is a U.S. National Stage Application of International Application No. PCT/FR2008/051815 filed Oct. 8, 2008, which claims priority to France Patent Application No. 0758193 filed Oct. 10, 2007. The contents of which are hereby incorporated by reference in their entirety.

The present invention relates to the field of molecularly imprinted polymers (MIPs) which are of use for the recognition of target molecules.

It relates more particularly to new MIPs which are suitable for the selective molecular recognition of glutathione GSH and/or of an analog thereof, and in particular which are of use for the treatment of media comprising in particular a mixture of glutathione GSH, and/or of an analog thereof, with GSH adducts.

Glutathione exists naturally in two chemical forms, namely the oxidized form (GSSG) and the reduced form (GSH) which represents approximately 98% to 99% of total glutathione.

Reduced glutathione (or γ-L-glutamyl-L-cysteinyl-glycine, denoted glutathione GSH or simply GSH) is a tripeptide synthesized by all the cells of the organism and constitutes the most abundant low-molecular-weight thiol (—SH)-comprising compound in eukaryote cells. It participates predominantly in cell defense mechanisms by virtue of its sulfhydryl function, which is responsible for its high reactivity and its powerful reducing capacity. Intracellular GSH concentration is thus considered by some authors to be a real marker of the state of health of an individual.

Consequently, GSH is used routinely for carrying out in vitro toxicology tests, as a chemical trapping agent which is of use for the characterization and the mechanistic study of reactive metabolites of active molecules.

By way of nonlimiting illustration of active molecules that can be subjected to such glutathione-based toxicology tests, mention may, for example, be made of food additives, plant-protection products, cosmetic active agents, drug candidates, human and veterinary drugs, and the active metabolites thereof.

For example, when a molecule is identified as potentially advantageous in therapy or for diagnosis, it is subjected to "early stage" toxicity tests in order to demonstrate as early as possible its possible toxicity and to allow laboratories to make a decision on its development as quickly as possible.

Preclinical prediction of drug candidates is, however, difficult, all the more so when the latter are associated with idiosyncratic reactions. Most drug candidates of this type form reactive metabolites, which can react with endogenous nucleophiles, like GSH.

Analysis of the covalent adducts formed between these metabolites and GSH provides information on the nature and the formation of these reactive metabolites. For this reason, the glutathione-based toxicology test involving these reactive metabolites has been adopted by a large number of pharmaceutical companies.

More specifically, the toxicology tests on drug candidates involving GSH consist in bringing together, on the one hand, the drug candidate and microsomes (allowing the formation of the principal metabolites of the drug candidate) and, on the other hand, a very large amount (generally from 20 to 500 times larger) of GSH, in order to generate the various adducts of GSH with the drug candidate and/or certain metabolites thereof. Quantification and determination of the nature and of the structure of the adducts formed from the drug candidate, and/or certain metabolites thereof, with GSH provide information that is vital to researchers responsible for investigating new drugs, and make it possible in particular to select the best drug candidates.

However, the presence of large amounts of glutathione (in GSH and GSSG form) in the associated analysis medium makes it very difficult, or even impossible, to separate, quantify and study the adducts formed during these toxicology tests, and analytical problems in exploiting the results are consequently encountered.

Several methods have already been developed in an attempt to improve the detection of the GSH adducts formed.

A first technique consists in using a radiolabeled drug candidate. According to this first method, the metabolites of the drug candidate will themselves also be radiolabeled and, consequently, their adducts with GSH will also be radiolabeled. The use of a chromatic system coupled with a radiosensitive detector then makes it possible to separate the drug candidate, the metabolites thereof and the adducts thereof with GSH from the glutathione molecules present in excess, the latter not being detected since they are not radiolabeled. This technique therefore involves the prior labeling of the drug candidates, which cannot always be done, and has the drawback of being expensive and relatively long to implement.

A second method, which is the one most widely used today, consists in using labeled glutathione (i.e. radiolabeled, fluorescent or chemically modified). According to this second method, when the GSH reacts with the drug candidate and/or certain metabolites thereof, it will form an adduct that is also labeled. However, this approach involves finding an analytical method for separating the labeled glutathione (generally present in an excess of 20- to 500-fold) from the labeled GSH adducts.

As radiolabeled glutathione, it is known practice to use titrated GSH, making it possible to directly quantify the peaks corresponding to the adducts. However, it is not easy to separate the GSH from the adducts thereof and the results are unsatisfactory from the point of view of sensitivity (Thompson, D. C. Chem. Res. Toxicol. 1995, 8, 55-60). Furthermore, the use of radiolabeled reagents implies special arrangements and specific management of waste, and also the purchasing of expensive reagents.

To obtain fluorescent glutathione, document US 2005/0186651 discloses, for its part, a method consisting in derivatizing the amine function of GSH with a dansyl group (denoted dGSH). However, it was observed that the acetominophenol metabolite adduct coelutes with the dGSH and that there is residual dGSH fluorescence owing to the high proportion of said dGSH. The presence of dGSSGd, which impairs analysis, was also detected and, for this reason, dithiothreitol (which can be a hindrance in the case of the study of disulfide formation with the candidate molecules) must also be added in order to prevent the formation of this dimer.

Finally, it is also known practice to use GSH modified with a quaternary ammonium (QA-GSH) in such a way as to semi-quantitatively quantify the GSH adducts (Soglia, J. R. Chem. Res. Toxicol. 2006, 19, 480-490). QA-GSH can thus be added to the samples derived from the toxicity tests before the analysis, as an internal standard.

In general, this second alternative, which requires the synthesis or the purchase of labeled GSH, also does not give complete satisfaction for analyzing GSH adducts.

There remains therefore a need for a simple, sensitive, rapid, relatively inexpensive, reliable method suitable for high-throughput screening tests which makes it possible to exploit the results of the abovementioned glutathione-based toxicology tests, while at the same time doing away with the labeling of the active molecule or of the GSH.

There remains in particular a need to facilitate the separation, detection and analysis of the GSH adducts formed during these tests, in order to evaluate the toxicity of an active molecule as rapidly as possible.

The present invention aims precisely to meet these needs.

Unexpectedly, the inventors have thus noted that it is possible to produce molecularly imprinted polymers (MIPs) dedicated to the selective recognition of glutathione GSH and/or of analogs thereof.

Thus, according to a first of its aspects, the present invention relates to a method for preparing a molecularly imprinted polymer (MIP) dedicated to the selective recognition of the reduced form of glutathione, GSH, or analog, comprising at least:
the copolymerization of a monomer or monomers intended to form the matrix of said molecular imprint with at least one monomer of general formula (I):

$$X-(R)_n-Y-G \qquad (I),$$

in which:
X represents a polymerizable monovalent group,
n is equal to 0 or 1,
R represents a saturated or unsaturated, linear, branched or cyclic $C_1$-$C_{10}$, in particular $C_1$-$C_5$, hydrocarbon-based chain, optionally interrupted with one or more heteroatoms chosen from N, O and S, and optionally substituted,
Y represents a function of a labile bond involving the sulfhydryl function of glutathione GSH or of an analog thereof,
G represents the residue of glutathione GSH or of a corresponding analog thereof,
under conditions favorable to the formation of said molecular imprint, and
the release of the residue G by cleavage of the bond function Y.

The invention also relates to the molecularly imprinted polymers (MIPs) that can be obtained by means of the method described above.

According to another of its aspects, the present invention relates to a molecularly imprinted polymer (MIP) comprising at least two recognition sites for a glutathione GSH entity and/or for an analog thereof, including at least one recognition site capable of interacting with the sulfhydryl function of said glutathione GSH entity and/or of a said analog thereof.

According to one variant embodiment, said recognition site is carried by an —S—S—Z unit, —S—Z being a residue intended to be displaced during the interaction of the glutathione GSH and/or of an analog thereof with said MIP, in particular during the interaction of the sulfhydryl —SH function of the glutathione GSH and/or of an analog thereof, with said recognition site. Z may, for example, be an optionally substituted aryl radical containing from 4 to 10 ring members, or an optionally substituted heteroaryl radical containing from 4 to 10 ring members, including 1 to 4 heteroatoms chosen from O, S, N and NR, with R representing H or alkyl, itself optionally substituted. Z may in particular represent According to yet another of its aspects, the present invention relates to a molecularly imprinted polymer (MIP) comprising:
one or more recognition sites for a glutathione GSH entity and/or for an analog thereof, and
at least one residue G as defined above,
said residue G being trapped in the cavity of said molecularly imprinted polymer via an interaction of its native sulfhydryl function with one of said recognition sites.

According to another of its aspects, the invention also relates to a method for treating a medium that may comprise, or comprises, at least glutathione GSH and/or an analog thereof, comprising at least:
(a) a step of bringing said medium into contact with at least one molecularly imprinted polymer in accordance with the invention, under conditions favorable to the extraction of the glutathione GSH and/or of analogs thereof, if present, by said molecular imprint,
(b) separation of said molecularly imprinted polymer, from the medium thus treated, and
(c) where appropriate, release of the glutathione GSH and/or of analogs thereof from said molecularly imprinted polymer resulting from step (b).

According to one embodiment, said medium may be a complex medium that may comprise, in addition to glutathione GSH and/or an analog thereof, at least one or more GSH adducts.

Thus, the MIPs in accordance with the present invention prove especially to be particularly advantageous from the analytical point of view when it is desired to detect the presence, or even to assay the amount, of GSH adducts formed in the presence of a large amount of GSH and/or of an analog thereof.

The MIP according to the invention, which is more particularly selective with respect to GSH and/or to an analog thereof, makes it possible to more selectively extract said GSH and/or analog thereof from such a medium and thus facilitates the subsequent characterization of the GSH adducts that may jointly exist therein.

The invention therefore also relates to the use of at least one molecularly imprinted polymer (MIP) in accordance with the invention, for the treatment of a medium that may comprise, or comprises, at least glutathione GSH and/or an analog thereof and GSH adducts.

In addition to this particularly advantageous application when glutathione-based toxicology tests are carried out, the MIPs according to the invention can also constitute a simple and easily used tool for assaying GSH and/or an analog thereof.

Thus, the invention also relates to the use of at least one molecularly imprinted polymer (MIP) in accordance with the invention for the purposes of extraction, detection, separation, purification, absorption, adsorption, retention or controlled release of the free form of glutathione GSH and/or of an analog thereof.

The advantages of the invention are, in addition, the advantages related to the use of molecularly imprinted polymers, namely high affinity and high selectivity, advantageous price, simplicity of preparation, chemical stability, mechanical stability and thermal stability, which enables the use thereof in particular under conditions where the cold chain is not observed, and long-term storage without loss of effectiveness.

DEFINITIONS

In the context of the present invention:
the term "adduct" is intended to mean a chemical species AB of which each molecular entity is formed by direct combination of two distinct molecular entities A and B,
the term "GSH adduct" is intended to mean an adduct formed by direct combination, on the one hand, of an active molecule (like, for example, a food additive, a plant-protection product, a cosmetic active agent, a drug candidate, or a human or veterinary drug) or of a metabolite thereof with, on the other hand, the sulfhydryl function of GSH or of an analog thereof,
the term "analog" is intended to mean a compound which has been subjected to a chemical modification, while at the same time maintaining its main structural characteristics, for instance its backbone. By way of chemical modifications, mention may in particular be made, for example, of the modification of one or more substituents, in particular for the purposes of labeling, or else the protection of reactive functions.

By way of analog of a compound, mention may also be made of the labeled forms, and in particular radiolabeled forms, of said compound. The labeling may in particular be carried out by means of a chromophore, for example a fluorescent chromophore, like dansyl for example,
the term "GSH analog" is intended to mean an analog as defined above, insofar as it conserves the native sulfhydryl function of GSH, in such a way that it can manifest, in the same way as GSH, the selective affinity for the MIPs according to the invention,
the term "function of a labile bond" is intended to mean a covalent bond that can be cleaved under relatively mild and/or selective conditions. A function of a labile bond can be broken selectively under conditions such that the breaking of the other covalent bonds is avoided. For example, a disulfide bond —SS— is capable of being broken in the presence of a thiol or else by selective irradiation by electromagnetic radiation at a specific wavelength, without causing any breaking of the other bonds, such as carbon-carbon, carbon-oxygen, carbon-sulfur or carbon-nitrogen bonds, that may also be present in the molecule, or by means of a reducing agent (for example, phosphine),
the term "recognition site" is intended to mean a site that exists in the cavity of the matrix of the MIP which is actually involved in the recognition of a species,
the term "complex medium" is intended to mean a medium comprising, in addition to the glutathione GSH and/or an analog thereof, at least one or more other supplementary entities such as, for example, one or more GSH adducts.

By way of example of a complex medium according to the invention, mention may in particular be made of a medium for incubating an active molecule used in a glutathione-based toxicology test, for instance a medium for incubating a drug candidate. In a complex medium of this type, the glutathione GSH and/or an analog thereof is present in very large amounts and is capable of hindering the analysis of the GSH adducts.

For the purpose of the invention, the expression "extraction of one (or more) species by molecular recognition of the species" is intended to mean a step during which the interaction of the species with the recognition sites of an MIP is sufficient to result in the formation of a complex composed of the MIP endowed, in all or some of its recognition sites, with said species.

For the purpose of the invention, the expression "release of one (or more) species" is intended to mean a step during which the complex form during the extraction of the species dissociates, for example following a modification of the oxidation, reduction, pH, salinity, temperature, flow rate, pressure or solvent polarity conditions, resulting in the presence of the target molecule(s) in a form free in solution.

For the purpose of the invention, the term "affinity" denotes the ability of a species to interact with a recognition site of an MIP. For the purpose of the invention, a strong affinity thus reflects the fact that this species has a strong ability for interacting with at least one recognition site of an MIP.

For the purpose of the invention, the term "interaction" is intended to mean the formation of weak bonds (for example of the type Van der Waals bonds, hydrogen bonds, pi donor-pi acceptor bonds, or hydrophobic interactions) and/or of strong bonds (for example of the type ionic bonds, covalent bonds, or else iono-covalent bonds, and preferably of the labile covalent bond type).

Molecularly Imprinted Polymer

The step of polymerization of the MIP around a template entity makes use of techniques known per se to those skilled in the art. Reference may thus be made to the article Peter A. G. Cormack et al., *Journal of Chromatography B*, 804 (2004) 173-182, which gives a review of the techniques available around aspects of MIP polymerization.

More specifically, two possible approaches (subsequently referred to as "conventional") mainly exist for producing MIPs: the covalent approach developed by Wulff in document U.S. Pat. No. 4,127,730 and the noncovalent approach developed by Mosbach in document U.S. Pat. No. 5,110,833. These two approaches can also be combined.

It is thus possible to use the first, covalent-type approach for the preparation of the MIP and the second approach for obtaining recognition by means of noncovalent interactions, as is, for example, disclosed in M. J. Whitcombe et al. "A New Method for the Introduction of Recognition Site Functionality into Polymers prepared by molecular Imprinting: Synthesis and Characterization of Polymeric Receptors for Cholesterol" *J. Am. Chem. Soc.*, 1995, 117, 7105-7111.

It is also possible to use the first and second approaches for the preparation of the MIP, and also for obtaining the recognition by means of covalent and noncovalent interactions simultaneously for the same target molecule. Thus, the interaction occurs at least at two distinct sites of the recognition site, as is, for example, disclosed in Wulff G. et al. *Macromol. Chem. Phys.* 1989, 190, 1717 and 1727.

A third approach (subsequently referred to as "semi-covalent") consists in using, for the synthesis of the MIPs, specific monomers according to the intended target molecule(s), and in particular at least partly monomers derived from a target molecule, thus playing partly the role of the polymer of the matrix and partly the role of the template entity. In other words, the purpose of a part of these monomers, once polymerized, is to be eliminated so as to give rise to the recognition sites.

The molecularly imprinted polymers suitable for implementation of the method according to the invention are precisely obtained according to this semi-covalent approach.

More specifically, they can be obtained by copolymerization of a monomer or monomers intended to form the matrix of said molecular imprint with at least one monomer of general formula (I):

(I), in which:
- X represents a polymerizable monovalent group,
- n is equal to 0 or 1,
- R represents a saturated or unsaturated, linear, branched or cyclic $C_1$-$C_{10}$, in particular $C_1$-$C_5$, hydrocarbon-based chain, optionally interrupted with one or more heteroatoms chosen from N, O and S, and optionally substituted,
- Y represents a function of a labile bond involving the sulfhydryl function of glutathione GSH and/or of an analog thereof,
- G represents the residue of glutathione GSH or of a corresponding analog thereof, under conditions favorable to the formation of said molecular imprint,
followed by release of the residue G by cleavage of the bond function Y.

According to one embodiment, X may represent a monovalent group chosen from vinyl, acrylic, methacrylic, allyl or styrene groups or any other unsaturated group capable of reacting via the free-radical process, and chemical groups enabling a polycondensation or sol-gel reaction.

It may in particular be a polymerizable group of vinyl, acrylic or methacrylic type, in particular an acrylic or methacrylic group, and preferably a methacrylic group.

According to one embodiment, R may represent a $C_1$-$C_4$, in particular $C_2$-$C_4$, and preferably $C_2$, linear hydrocarbon-based chain.

According to one embodiment, Y may represent a disulfide function —SS—.

According to one embodiment, G may represent a residue of a glutathione analog, preferably N-boc-glutathione.

As monomer of general formula (I), mention may in particular be made of N-boc-glutathione disulfide methacrylate of which is derived from glutathione disulfide methacrylate, itself derived from glutathione.

The molecularly imprinted polymer according to the present invention is capable of being obtained by copolymerization, in addition, of at least one other monomer, in particular chosen from crosslinking agents.

As crosslinking agent, mention may in particular be made of p-divinylbenzene (DVB), 1,3-diisopropenyl-benzene (DIP), ethylene glycol dimethacrylate (EGDMA), tetramethylene dimethacrylate (TDMA), N,O-bisacryloyl-L-phenylaninol, 2,6-bisacryloylamidopyridine, 1,4-phenylenediacrylamide, N,N'-1,3-phenylenebis(2-methyl-2-propenamide (PDBMP), 3,5-bisacrylamidobenzoic acid, 1,4-diacryloylpiperazine (DAP), N,N'-amethylenebis-acrylamide (MDAA), N,N'-ethylenebismethacrylamide, N,N'-tetramethylenebismethacrylamide, N,N'-hexamethylenebismethacrylamide, anhydroerythritol dimethacrylate, 1,4-; 3,6-dianhydro-D-sorbitol-2,5-dimethacrylate, isopropylenebis(1,4-phenylene)dimethacrylate, trimethylpropane trimethacrylate (TRIM), pentaerythritol triacrylate (PETRA) and pentaerythritol tetraacrylate (PETEA).

The crosslinking agent is preferably chosen from ethylene glycol dimethacrylate and divinylbenzene.

The molecular imprint can be synthesized by solution polymerization, emulsion polymerization, suspension polymerization, precipitation polymerization, microemulsion polymerization or dispersed-phase polymerization, or under conditions for preparing microgels.

The matrix of the molecular imprint formed may be of polyacrylate, polymethyacrylate, polyacrylamide, polyvinyl, polyacrylein, polyacrylonitrile, poly(vinyl alcohol), poly(alkyl vinyl ketone), polybenzothiazole, bisphenol A polycarbonate, poly(diallyldimethylammonium chloride), poly(vinyl chloride), polysiloxane, aromatic polyether, polyethersulfone, polyetherimide, polyethyleneimine, polyimide, polyimidazole, polyoxymethylene, polyoxazole, polyoxyphenylene, polyoxytetramethylene, poly(vinyl alkyl ether), polyvinylpyrrolidone and poly(vinyl methyl ketone) nature.

The MIPs that can be obtained by copolymerization of at least one monomer of general formula (I) as defined above exhibit a more selective recognition for glutathione GSH and/or for analogs thereof than MIPs obtained according to a conventional approach. This aspect is in particular illustrated by example 5, which demonstrates the considerable difference in selectivity between a MIP synthesized according to the conventional approach and a MIP according to the invention.

Moreover, as also emerges from this comparative example, and also from example 6, the MIPs in accordance with the invention also exhibit a more selective recognition for glutathione GSH and/or analogs thereof than for GSH adducts.

The use of a monomer of general formula (I) as defined above in fact makes it possible to confer, on the cavity of the MIP which forms during the polymerization, an internal conformation close to that of the molecule of GSH or of an analog thereof having served as template entity. Consequently, the GSH adducts (which lack the native sulfhydryl function of GSH and of analogs thereof, given that it is precisely this function which is involved in their formation) will exhibit an interaction with the MIP in accordance with the invention that will be less selective than that of GSH and/or of an analog thereof, with this same MIP.

Method

As indicated previously, the invention also relates to a method for treating a medium that may comprise, or comprises, the free form of glutathione GSH and/or an analog thereof and at least one or more GSH adducts, comprising at least:
(a) a step of bringing said medium into contact with at least one molecularly imprinted polymer in accordance with the invention, under conditions favorable to the extraction of the glutathione GSH and/or of analogs thereof, if present, by said molecular imprint,
(b) separation of said molecularly imprinted polymer from the medium thus treated, and
(c) where appropriate, release of the glutathione GSH and/or of analogs thereof from said molecularly imprinted polymer resulting from step (b).

At the end of step (b), a purified medium, i.e. a medium that is significantly depleted, or even devoid, of GSH and/or of an analog thereof, is therefore obtained.

Where appropriate, the entities having no interaction with the MIP, and for example the drug candidate, may remain in the purified medium.

According to one embodiment, step (b) can be followed by specific release of the GSH and/or analogs thereof.

According to one particular embodiment of the invention, the medium treated may be a medium for incubating an active molecule used in a glutathione-based toxicology test, for example as defined above.

The above method according to the invention may be followed by qualitative and/or quantitative analysis of the treated medium obtained at the end of step (b), for the characterization of the GSH adducts according to any method known to those skilled in the art.

According to one variant embodiment, the method according to the invention may also comprise, as a preliminary to step (a), at least:

(i) a step of bringing a "complex" medium, that may comprise, in addition to the glutathione GSH and/or an analog thereof, at least one or more GSH adduct(s), into contact with at least a first molecularly imprinted polymer capable of interacting with the GSH adducts, and the glutathione and analogs thereof, under conditions suitable for extraction of the GSH adducts, of the glutathione and of analogs thereof, (ii) separation of said molecularly imprinted polymer from the medium thus treated, and (iii) formation of a medium enriched in said GSH adducts, in said glutathione and in said analogs thereof, by release of the GSH adducts, of the glutathione and of analogs thereof from the molecularly imprinted polymer resulting from step (ii).

This medium may subsequently undergo step (a) of the method according to the invention.

The MIPs can be used on any appropriate support.

For the purpose of the invention, the term "support" is intended to mean very broadly any flexible or rigid solid substrate on or in which the MIPs are capable of being bound, adhesively bonded, deposited, synthesized in-situ, filled and/or packaged.

The supports that can be used according to the invention may be of any nature, for instance of biological, nonbiological, organic or inorganic nature, or else a combination thereof. They may be in any form, and in particular take the form of particles, gels, sheets, tubes, spheres, capillaries, tips, films or wells, of any size and of any shape.

They may, for example, be in the form of particles of homogeneous size, in particular between 10 nm and 10 mm, preferably between 25 and 45 µm, capable of being consequently packaged in the form of a cartridge.

In general, the MIPs can, for example, be used on or in a support chosen from an SPE cartridge, a multi-well plate, for instance a 96-well plate, a patch, a teabag, a microtube, an HPLC column, a strip, chips, slides, silica plates, thin layers, a porous surface, a nonporous surface and a microfluidic system.

According to one embodiment of the invention, the molecularly imprinted polymers can be used on an extraction column, for example an SPE cartridge.

Thus, according to one embodiment of the invention, the method can comprise at least one solid-phase extraction (SPE) step.

A solid-phase extraction procedure generally comprises three or four steps. The first is the conditioning of the adsorbent contained in the extraction cartridge, which makes it possible to wet the support, solvating the functional groups present at its surface. During the second step, the solution to be treated is percolated through the MIP, such that the entities having no affinity with the latter are not retained. On the other hand, the target molecule(s), and possibly other entities having a strong affinity with the adsorbent, remain on the support at the end of this step.

An additional washing step can be carried out in order to remove the entities weakly retained (the drug candidate, for example) by the support, by means of a solvent having an eluent strength suitable for eluting these entities while at the same time keeping the target molecule(s) on the support.

If necessary, the elution of the target molecule(s) can finally be carried out by passing a solvent specifically chosen so as to break the recognition interactions involved between the target molecule(s) and the MIP, while at the same time avoiding eluting interfering entities strongly retained on the support, so as to release the extracted target molecule(s).

At the end of this extraction and release process, a purified solution, optionally enriched in target molecule(s), can therefore be obtained.

For example, in the case of an application of the method of the invention for the purposes of treating a medium used in a glutathione-based toxicology test, the advantage is that of retaining the target molecules of the MIP in accordance with the invention (namely, glutathione GSH and/or analogs thereof) on the support and obtaining an eluted solution which comprises the GSH adducts (retained less selectively on the support) and which is depleted of glutathione GSH and/or of analogs thereof.

Typically, the solvents used in a solid-phase extraction can be organic solvents, for instance acetonitrile, methanol or dichloromethane, or aqueous solvents, for instance water, or buffer solutions, it being possible for the solvents to be used as a mixture and with various salinity, pH and polarity conditions.

Other types of pretreatment steps can be envisioned, for instance solid-phase microextraction (SPME), solid-phase dynamic extraction (SPDE), stir bar sorption extraction (SBSE), or capillary or strip or chip extraction.

According to one variant embodiment, before it is used in the medium to be treated, the cavity of the MIP in accordance with the invention may contain a covalently or noncovalently attached molecule different than GSH or than an analog thereof, for example a label, and which is intended to be displaced by the GSH and/or an analog thereof when said GSH and/or analog thereof interacts with its recognition site.

The label may in particular be detected, for example after release, by visible colorimetry, for instance with the naked eye, by radiochemistry, by nuclear medicine, for instance by scintigraphy, by imaging, by resonance (MRI), by X-rays, by light scattering, by mass spectrometry, by spectroscopy, for example by fluorescence spectroscopy or UV-visible spectroscopy, by ultrasound, by radioactivity, by refractometry, by optical detection, piezoelectric detection or acoustic detection, by electrochemistry, by conductivity, by pH-metry, or else biologically, and preferably with the naked eye.

The examples which appear hereinafter are present by way of nonlimiting illustration of the field of the invention.

EXAMPLES

Two MIPs recognizing GSH were prepared, one by a conventional approach and the other by a semi-covalent approach, and the recognition properties thereof with respect to GSH were demonstrated.

Example 1

Synthesis of Molecularly Imprinted Polymers According to the Noncovalent "Conventional" Approach a) Synthesis of the Target Molecule N—BOC-GS—Ac γ-L-glutamyl-S-acetyl-L-cysteinyl-glycine (GS—Ac)

In a round-bottomed flask surmounted by a condenser, 5 g of glutathione (16.3 mmol) are dissolved in 55 ml of trifluoroacetic acid. The assembly is placed under nitrogen and nitrogen is bubbled into the solution for 5 minutes. Once the round-bottomed flask has been placed under nitrogen, 2 ml of acetic acid are added. The mixture is brought to 40° C. for 20 minutes. At ambient temperature, 1.5 ml of water are added and the resulting mixture is then heated at 40° C. for 20 minutes. The mixture is then evaporated by vacuum pump and then ethyl acetate is added. The product precipitates in the form of a sticky paste. The product is then solubilized in the minimum amount of hot water and then acetone is added. The resulting mixture is placed at 4° C. for 3 days. The white product which has precipitated is filtered off. 3.38 g of expected product are recovered.

Yield: 59%.

$^1$H NMR (DMSO-$d_6$, 300 MHz) δ 1.82 (m, 2H, $CH_2$(Glu)), 2.32 (m, 5H, Me and $CH_2$—C(O) (Glu), 2.96 (dd, J=9.4 and 13.4 Hz, CHS, 1H), 3.33-3.39 (dd and t, 2H, CHS and CHNC(O) (Glu)), 3.70 (d, J=5.46 Hz, 2H, N—$CH_2$—C(O) (Gly)), 4.37-4.45 (m, 1H, CHN (Cys)), 8.51 (d, J=8.5 Hz, NH (Cys), 1H), 8.64 (t, J=5.6 Hz, NH (Gly), 1H).

ESI-MS (negative mode)=348.27 ([M–H]$^-$).

γ-L-N—BOC-glutamyl-S-acetyl-L-cysteinyl-glycine (N—BOC-GS—Ac)

2 g of γ-L-glutamyl-S-acetyl-L-cysteinyl-glycine (5.76 mmol) are suspended in 13 ml of dioxane. 13 ml of water are added, followed, dropwise, by an aqueous solution of $K_2CO_3$ (791 mg, 1 eq. in 13 ml of water). An effervescence occurs. $BOC_2O$ dissolved in 2 ml of dioxane is added at 0° C. The solution turns cloudy and then becomes clear. It is stirred for 2 hours at ambient temperature. The medium is evaporated and then ethyl acetate is added. A 4% aqueous solution of $NaHSO_4$ in water is added so as to be between pH 2 and pH 3. The aqueous phase is extracted three times with ethyl acetate. The organic phase is then washed with water and it is then dried over $MgSO_4$. 1.2 g of a white product are obtained.

Yield: 46%.

$^1$H NMR ($CD_3CN$, 300 MHz) δ 1.33 (s, 9H, tBu), 1.76-2.02 (m, 2H, $CH_2$(Glu)), 2.24 (m, 5H, Me and $CH_2$—C(O) (Glu), 3.03 (dd, J=8.1 and 13.92 Hz, CHS, 1H), 3.29 (dd, J=4.89 and 13.95 Hz, CHS, 1H), 3.81 (d, J=5.85 Hz, 2H, N—$CH_2$—C(O) (Gly)), 4.03 (m, 1H, CHN), 4.46 (m, 1H, CHN), 5.79 (d, J=7.74 Hz, NH (BOC), 1H), 6.99 (d, J=7.92 Hz, NH (Cys), 1H), 7.18 (t, J=5.64 Hz, NH (Gly), 1H).

ESI-MS (negative mode)=448.40 ([M–H]$^-$)

b) Synthesis of the Corresponding Imprinted and Non-Imprinted Materials No. 1 (Conventional Approach)

The ethylene glycol dimethyl acrylate is washed several times with a saturated basic solution of NaCl, so as to remove the inhibitor. It is dried over $MgSO_4$. The initiator azobisisobutyronitrile (AIBN) is recrystallized from acetone.

The imprinted material (imprint) No. 1 is prepared by mixing 279 mg of N—BOC-GS—Ac, 4.9 g of ethylene glycol dimethyl acrylate, 551 mg of 2-carboxyethyl acrylate and 131 mg of 4-vinylpyridine in 6.9 ml of anhydrous acetonitrile. The mixture is degassed by bubbling nitrogen for 10 minutes and then 57 mg of AIBN are added. The polymerization is carried out at 50° C. for 72 hours so as to form a colored monolith.

The non-imprinted material No. 1 is prepared by mixing 5.0 g of ethylene glycol dimethyl acrylate, 524 mg of 2-carboxyethyl acrylate and 143 mg of 4-vinylpyridine in 6.9 ml of anhydrous acetonitrile. The mixture is degassed by bubbling nitrogen for 10 minutes and then 57 mg of AIBN are added. The polymerization is carried out at 50° C. for 72 hours so as to form a colored monolith.

The matrices prepared above are ground and then screened. The particles of which the size is between 25 and 45 µm are introduced into a 150×4.6 mm HPLC column and then compacted by pressing and washed with a mixture of 5% acetic acid in acetonitrile/$H_2O$ (97.5/2.5), then with acetonitrile, so as to study the recognition in HPLC. There are thus 2 HPLC columns.

Example 2

Synthesis of Molecularly Imprinted Polymers According to the Semi-Covalent Approach a) Synthesis of a Glutathione-Derived Monomer

A monomer called N-Boc glutathione disulfide methacrylate was synthesized in 4 steps, with an overall yield of 13%.

The first step is described by several authors, and in particular Lapeyre et al. The second step is described by Bulmus et al., with a yield of 35% by mass; the procedure was slightly modified, and the product was obtained with a yield of 63%. The third step made it possible to obtain the glutathione-derived monomer quantitatively. The final step is the protection of the amine function with a t-butylcarbamate group.

with dichloromethane with a slight ethyl acetate gradient). Only the cleanest fractions are evaporated.

Yield: 41% (colorless oil).
Rf=0.48 (80/20 DCM/EtOAc)

2-Pyridin-2-yldisulfanylethanol $^1$H NMR (CDCl$_3$, 300 MHz) δ 2.83 (t, J=5.46 Hz, 2H, CH$_2$S), 3.69 (t, J=5.25 Hz, 2H, CH$_2$O), 5.42 (bs, OH, 1H), 6.99-7.04 (m, 1H), 7.36 (m, 1H), 7.45-7.51 (m, 1H), 8.34 (m, 1H).

Pyridyl Disulfide Methacrylate 2.25 g of bis(2-pyridyl)disulfide are dissolved in 100 ml of pyridine:methanol (1:99). β-mercaptoethanol (700 μl, 1 eq.) is added dropwise to the solution. An immediate yellow color is observed. The medium is stirred overnight. The following day, starting product is no longer observed, and the solution is evaporated. The residue is passed over two silica columns, so as to obtain 770 mg of the expected product (column prepared The disulfide (770 mg) and then triethylamine (860 μl, 1.5 eq.) are added to 50 ml of DCM. Methacryloyl chloride (400 μl, 1.2 eq.) is added dropwise, at 0° C. The solution is stirred at 0° C. for 30 minutes. The solution is stirred at ambient temperature overnight. The organic phase is washed three times with water and three times with a saturated solution of NaHCO$_3$. The organic phase is dried over MgSO$_4$ and is evaporated. The residue is passed over a silica column. The column is packed with cyclohexane and, once the residue has been loaded, elution is carried out with dichloromethane. A fraction of the expected product is recovered (660 mg).

Yield: 63%.

Rf=0.84 (80/20 DCM/EtOAc).

$^1$H NMR (CDCl$_3$, 300 MHz) δ 1.82 (s, Me, 3H), 2.99 (t, J=6.36 Hz, CH$_2$S), 4.28 (t, J=6.36 Hz, 2H, CH$_2$O), 5.47 (s, CH=, 1H), 6.01 (s, CH=, 1H), 6.98 (m, 1H), 7.49-7.61 (m, 2H), 8.34 (d, J=4.8 Hz, 1H).

$^{13}$C NMR (CDCl$_3$, 75 MHz) δ 18.54 (Me), 37.64 (SCH$_2$), 62.63 (OCH$_2$), 119.91 (CH), 121.14 (CH), 126.31 (=CH$_2$), 136.16 (C$^{IV}$), 137.39 (CH), 149.91 (CH), 159.95 (C$^{IV}$), 167.15 (C$^{IV}$).

HPLC conditions No. 1: $t_R$=15.98 min; $t_R$ (pyridylthione)= 5.03 min.; $t_R$ (GSH)=3.7 min.

HPLC conditions No. 1: Hypersil Gold 100×4.6 mm column. Injection of 5 μl. 1 ml/min. Gradient: 0.1% TFA in water for 2 minutes and then 80/20 ACN/0.1% TFA-water up to 20 minutes then constant up to 25 minutes.

Glutathione Disulfide Methacrylate Monomer

820 mg of the pyridyl disulfide methacrylate monomer are solubilized in 10 ml of ACN, then 2.6 ml of DMF, and then 15 ml of water. 1.1 equivalents of GSH (1.09 g) are added. Coloration of the solution owing to the release of pyridylthione is very rapidly observed. After stirring for 5 minutes, the solution is diluted in the same volume of water and then freeze-dried overnight. A light yellow powder is then obtained. The powder is washed with 4 times 50 ml of acetonitrile until the filtrate is colorless. A white powder is then obtained, which is dried under vacuum. 1.48 g of product are obtained.

Quantitative Yield.

ESI-MS (positive mode)=452.07 ([M−H]$^+$), 902.8 ([2M+H]$^+$]).

HPLC conditions No. 1: $t_R$=10.85 min.; $t_R$ (pyridylthione)= 5.03 min.; $t_R$ (GSH)=3.7 min.

N-Boc Glutathione Disulfide Methacrylate Monomer 500 mg of the glutathione disulfide methacrylate monomer are solubilized in 2 ml of dioxane, 1 ml of water and 306 mg of K$_2$CO$_3$ diluted in 2 ml of water. 4 ml of water and 3 ml of dioxane are added to the suspension. 1.1 equivalents of BOC$_2$O are added at 0° C. The mixture is left to stir at ambient temperature for 30 minutes. The medium is evaporated under vacuum. Ethyl acetate is added and the mixture is acidified under cold conditions with a 4% aqueous solution of KHSO$_4$, to pH 2. The resulting product is extracted twice with ethyl acetate. 351 mg of a slightly yellow oil are obtained.

Yield: 52%.

HPLC conditions No. 1: $t_R$=19.1 min.; $t_R$ (pyridylthione)= 5.03 min.; $t_R$ (GSH)=3.7 min.

ESI-MS (negative mode)=550.07 ([M−H]$^−$).

b) Synthesis of the Corresponding Imprinted and Non-Imprinted Materials No. 2 (Semi-Covalent Approach)

The ethylene glycol dimethyl acrylate is washed several times with a saturated basic solution of NaCl so as to remove the inhibitor. It is dried over MgSO$_4$. The initiator azobisisobutyronitrile (AIBN) is recrystallized from acetone.

The imprinted material (imprint) No. 2 is prepared by mixing 344 mg of N-Boc glutathione disulfide methacrylate monomer, 4.96 g of ethylene glycol dimethyl acrylate, 540 mg of 2-carboxyethyl acrylate and 131 mg of 4-vinylpyridine in 6.9 ml of anhydrous acetonitrile. The mixture is degassed by bubbling nitrogen for 10 minutes and then 57 mg of AIBN are added. The polymerization is carried out at 50° C. for 72 hours so as to form a colored monolith.

The non-imprinted material No. 2 is prepared by mixing 5.0 g of ethylene glycol dimethyl acrylate, 540 mg of 2-carboxyethyl acrylate, 81 mg of 2-hydroxyethyl methacrylate and 131 mg of 4-vinylpyridine in 6.9 ml of anhydrous acetonitrile. The mixture is degassed by bubbling nitrogen for 10 minutes and then 57 mg of AIBN are added. The polymerization is carried out at 50° C. for 72 hours so as to form a colored monolith.

The matrices prepared above are ground and then screened. The particles of which the size is between 25 and 45 μm are introduced into a 150×4.6 mm HPLC column and then compacted by pressing. The two columns are placed in series and in a closed circuit in a 50/50 solution of MeCN/phosphate buffer, pH=10 (Merck solution) containing 300 mg of DTT, for 48 hours. The columns are then washed with water and then with ACN, for studying the recognition in HPLC. There are thus 2 HPLC columns.

Example 3

Evaluation of the Recognition by the Material No. 1 (Conventional Approach)

Two solutions, 2 mM and 5 mM, of glutathione in water are injected onto the two columns packed, respectively, with the imprint No. 1 and with the non-imprinted material No. 1.

The eluent used is a 90/10 mixture of acetonitrile/10 mM buffer at various pH values, with a flow rate of 1 ml/min. The glutathione is detected with a light scattering detector (ELSD). The injection volumes are 20 μl.

The k' (capacity factor) and IF (imprint factor) values are determined for evaluating the recognition of glutathione on the matrices.

| Analyte | $k'_{MIP\ No.\ 1}$ | $k'_{non\text{-}imprinted\ material\ No.\ 1}$ | IF |
|---|---|---|---|
| 2 mM glutathione | 5.48 | 1.52 | 3.60 |
| 5 mM glutathione | 5.58 | 1.50 | 3.71 |

HPLC conditions: Glutathione, eluent: 90/10 1% AA ACN/H₂O, particles 25-45 μm.

Under the analytical conditions used, substantial recognition by the imprint No. 1 is observed for glutathione at high concentrations.

Example 4

Evaluation of the Recognition by the Material No. 2 (Semi-Covalent Approach)

Two solutions, at 4.5 mM and at 2.2 mM, of glutathione in an 85/15 solution of MeCN/water are injected onto the two columns packed, respectively, with the imprint No. 2 and with the non-imprinted material No. 2.

The eluent used is a mixture containing acetonitrile/water with various percentages and in the presence or absence of acetic acid, with a flow rate of 1 ml/min. The glutathione is detected with a light scattering detector (ELSD). The injection volumes are 20 μl.

The k' (capacity factor) and IF (imprint factor) values are determined for evaluating the recognition of glutathione on the matrices.

|  | 90/10 (1% AA ACN/H₂O) | | 90/10 (0.5% AA ACN/H₂O) | |
|---|---|---|---|---|
|  | Imprint No. 2 | Non-imprinted material No. 2 | Imprint No. 2 | Non-imprinted material No. 2 |
| 4.5 mM GSH | 12.776 | 4.643 | 17.149 | 5.735 |

| Analyte | $k'_{MIP\ No.\ 1}$ | $k'_{non\text{-}imprinted\ material\ No.\ 1}$ | IF |
|---|---|---|---|
| 4.5 mM glutathione | 9.09 | 2.19 | 4.16 |

HPLC conditions: eluent: 90/10 0.5% AA ACN/H₂O, particles 25-45 μm.

Under the analytical conditions used, substantial recognition by the imprint No. 2 is observed for glutathione at high concentrations. This recognition is greater than that by the imprint No. 1.

Example 5

Comparison

Various solutions of GSH and of GSH adducts in an 85/15 solution of MeCN/water are injected onto the two columns packed, respectively, with the imprint No. 1 and with the imprint No. 2.

The eluent used is a mixture containing 1% acetic acid acetonitrile/water with a ratio of 90/10, with a flow rate of 1 ml/min. The glutathione and the adducts are detected with an ELSD. The injection volumes are 20 μl.

The k' (capacity factor) and selectivity values are determined for evaluating the recognition of the glutathione GSH and of the GSH adducts on the imprints.

GSH

Adduct 1

Adduct 2

Adduct 3

|  | Retention time | Mid-height width | k' | Selectivity |
|---|---|---|---|---|
| 90/10 (1% AA ACN/H₂O): Imprint No. 1 | | | | |
| 5.07 mM GSH | 9.213 | 1.8 | 4.42 | 100 |
| 2 mM GSH | 9.078 | 1.7 | 4.34 | 98 |

| | | | | |
|---|---|---|---|---|
| 5.91 mM adduct 1 | 7.693 | 3.2 | 3.55 | 80 |
| 4.48 mM adduct 2 | 9.823 | 2.2 | 4.78 | 108 |
| 90/10 (1% AA ACN/H$_2$O): Imprint No. 2 | | | | |
| 2.3 mM GSH | 11.214 | 4.5 | 7.01 | 100 |
| 3.7 mM adduct 1 | 7.406 | 1.5 | 4.29 | 61 |
| 2.4 mM adduct 2 | 7.893 | 1.6 | 4.64 | 66 |

Figure 1A:
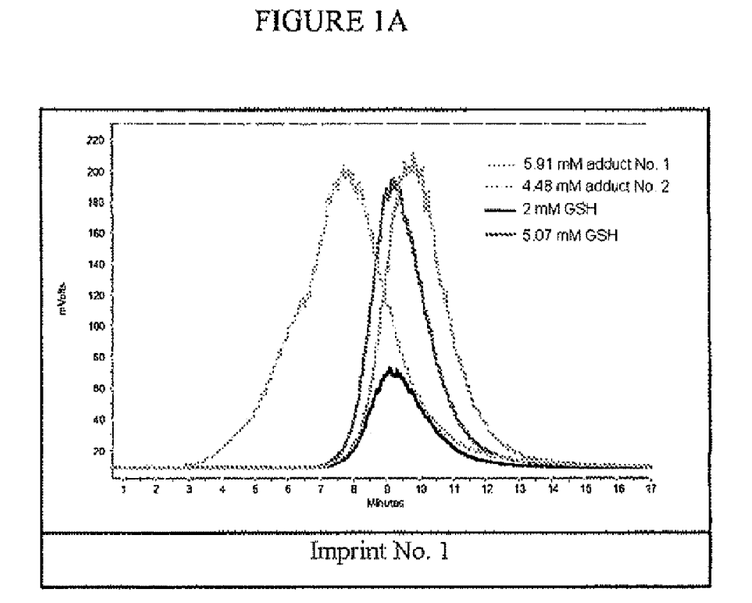
FIGS. 1A and 1B are graphs depicting experimental results.
Figure 1B:
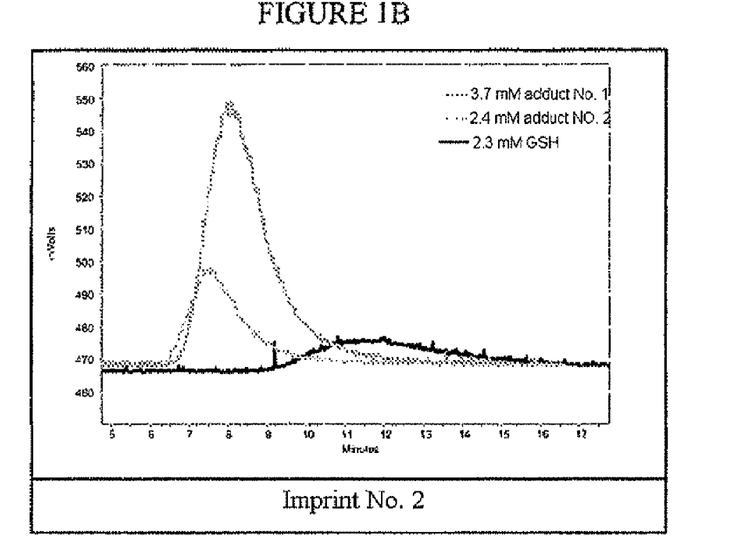

These results are respectively illustrated by FIGS. 1A and 1B.

When glutathione is injected onto the two imprints, the glutathione leaves more rapidly on the imprint No. 1 and the peak is not as wide. Moreover, the imprint No. 1 is not very selective with respect to the adducts.

Furthermore, it is noted that the imprint No. 2 is more selective for glutathione than the imprint No. 1.

Example 6

Recognition and Selectivity of the Imprint No. 2 with Respect to GSH Adducts by SPE An SPE cartridge is prepared by introducing 200 mg of the imprint No. 2 between two frits. Prior to extraction, 5 ml of acetonitrile and 6 ml of a solution containing 90/10 ACN (1% AA)/H$_2$O are passed over the cartridge in order to condition it before introducing the solution to be percolated. Then, 1 ml of a solution containing 182.89 µg of GSH (0.60 mM), 5.8 µg of adduct 2 (0.015 mM) and 4.14 µg of adduct 3 (0.009 mM) in 90/10 MeCN (1% AA)/water is percolated through the SPE cartridge. Several 500 µl fractions of a solution containing 90/10 MeCN (1% AA)/water are used as washing solution. 3 ml of an 85/15 solution of ACN/H$_2$O are then percolated. The various fractions are subsequently analyzed by HPLC-UV.

The following table gives the recovery rates (%) for adducts 2 and 3 and for GSH obtained during this extraction.

| Fraction | % recovery rate for adduct 3 | % recovery rate for adduct 2 | % recovery rate for GSH |
|---|---|---|---|
| Percolation | 0 | 0 | 0 |
| Wash 1 | 0 | 0 | 0 |
| Wash 2 | 0 | 0 | 0 |
| Wash 3 | 0 | 30 | 0 |
| Wash 4 | 29 | 42 | 3 |
| Wash 5 | 33 | 20 | 8 |
| Wash 6 | 21 | 8 | 12 |
| 3 ml ACN/H$_2$O 85/15 | 13 | 0 | 72 |

Under these conditions of use, a difference in behavior of the matrix of the imprint No. 2 with respect to the GSH adducts and to GSH is observed.

The adducts are not retained in the wash solutions and a large part of the glutathione (72%) could be removed from the sample.

CONCLUSION

The MIP prepared by a conventional approach exhibits a recognition both for GSH and for its adducts, whereas the MIP prepared by a semi-covalent approach exhibits a greater recognition for GSH, and therefore better selectivity.

The MIP obtained using a semi-covalent approach can make it possible to carry out a pretreatment step before the analysis of the incubation media. This pretreatment step makes it possible to selectively remove GSH, while at the same time conserving the GSH adducts in the pretreated solution, and thus to carry out a purification, and optionally an enrichment, of GSH adducts.

The invention claimed is:

1. A method for preparing a molecularly imprinted polymer (MIP) dedicated to the selective recognition of the reduced form of glutathione, GSH, or analog, comprising at least:
   the copolymerization of a monomer or monomers intended to form the matrix of said molecular imprint with at least one monomer of general formula (I):

$$X\text{—}(R)_n\text{—}Y\text{-}G \qquad (I),$$

in which:
   X represents a polymerizable monovalent group,
   n is equal to 0 or 1,
   R represents a saturated or unsaturated, linear, branched or cyclic C$_1$-C$_{10}$ hydrocarbon-based chain, optionally interrupted with one or more heteroatoms chosen from N, O and S, and optionally substituted,
   Y represents a function of a labile bond involving the sulfhydryl function of glutathione GSH or of an analog thereof,
   G represents the residue of glutathione GSH or of a corresponding analog thereof,
   under conditions favorable to the formation of said molecular imprint, and
   the release of the residue G by cleavage of the bond function Y.

2. The method as claimed in claim 1, wherein X represents a monovalent group chosen from vinyl, acrylic, methacrylic, allyl or styrene groups or any other unsaturated group capable of reacting via the free-radical process, and chemical groups enabling a polycondensation or sol-gel reaction.

3. The method as claimed in claim 1, wherein Y represents a disulfide function —SS—.

4. The method as claimed in claim 1, wherein at least one monomer of general formula (I) is N-boc-glutathione disulfide methacrylate.

5. A molecularly imprinted polymer (MIP) that can be obtained by means of the method as claimed in claim 1.

6. A molecularly imprinted polymer (MIP) comprising at least two recognition sites for a glutathione GSH entity and/or for an analog thereof, including at least one recognition site capable of interacting with the sulfhydryl function of said glutathione GSH entity and/or of a said analog thereof.

7. The molecularly imprinted polymer as claimed in claim 6, wherein said recognition site is carried by an —S—S—Z unit, —S—Z being a residue intended to be displaced during the interaction of the glutathione GSH and/or of an analog thereof with said molecularly imprinted polymer.

8. A molecularly imprinted polymer (MIP) comprising:
   one or more recognition sites for a glutathione GSH entity and/or for an analog thereof, and
   at least one residue of glutathione GSH or of a corresponding analogue thereof,
   said residue being trapped in the cavity of said molecularly imprinted polymer via an interaction of its native sulfhydryl function with one of said recognition sites.

9. A method for treating a medium that may comprise, or comprises, at least glutathione GSH and/or an analog thereof, comprising at least:
   (a) a step of bringing said medium into contact with at least one:
   molecularly imprinted polymer obtained according to claim 5, molecularly imprinted polymer (MIP) comprising at least two recognition sites for a glutathione GSH entity and/or for an analog thereof, including at least one recognition site capable of interacting with the sulfhydryl function of said glutathione GSH entity and/or of a said analog thereof, or molecularly imprinted polymer (MIP) comprising:
  one or more recognition sites for a glutathione GSH entity and/or for an analog thereof, and
  at least one residue of glutathione GSH or of a corresponding analogue thereof,
    said residue being trapped in the cavity of said molecularly imprinted polymer via an interaction of its native sulfhydryl function with one of said recognition sites,
  under conditions favorable to the extraction of the glutathione GSH and/or of analogs thereof, if present, by said molecular imprint, (b) separation of said molecularly imprinted polymer from the medium thus treated, and (c) where appropriate, release of the glutathione GSH and/or of analogs thereof from said molecularly imprinted polymer resulting from step (b).

10. The method as claimed in claim 9, wherein the molecularly imprinted polymer is used on an extraction column, for example an SPE cartridge.

11. The method as claimed in claim 9, wherein said medium is a complex medium that may comprise, in addition to glutathione GSH and/or an analog thereof, at least one or more GSH adduct(s).

12. The method as claimed in claim 11, further comprising as a preliminary to step (a), at least:
  (i) a step of bringing said medium into contact with at least a first molecularly imprinted polymer capable of interacting with the GSH adducts, and the glutathione and analogs thereof, under conditions suitable for extraction of the GSH adducts, of the glutathione and of analogs thereof,
  (ii) separation of said molecularly imprinted polymer from the medium thus treated, and
  (iii) formation of a medium enriched in said GSH adducts, in said glutathione and in said analogs thereof, by release of the GSH adducts, of the glutathione and of analogs thereof from the molecularly imprinted polymer resulting from step (ii).

13. The method as claimed in claim 11, wherein the complex medium is a medium for incubating an active molecule used in a glutathione-based toxicology test.

14. A method for the extraction, detection, separation, purification, absorption, adsorption, retention or controlled release of the free form of glutathione GSH and/or of an analog thereof comprising the use of at least one:
  molecularly imprinted polymer obtained according to claim 5,
  molecularly imprinted polymer (MIP) comprising at least two recognition sites for a glutathione GSH entity and/or for an analog thereof, including at least one recognition site capable of interacting with the sulfhydryl function of said glutathione GSH entity and/or of a said analog thereof, or
  molecularly imprinted polymer (MIP) comprising:
    one or more recognition sites for a glutathione GSH entity and/or for an analog thereof, and
    at least one residue of glutathione GSH or of a corresponding analogue thereof,
    said residue being trapped in the cavity of said molecularly imprinted polymer via an interaction of its native sulfhydryl function with one of said recognition sites.

15. A method for the treatment of a medium that may comprise, or comprises, at least glutathione GSH and/or an analog thereof and GSH adducts comprising the use of at least one:
  molecularly imprinted polymer obtained according to claim 5,
  molecularly imprinted polymer (MIP) comprising at least two recognition sites for a glutathione GSH entity and/or for an analog thereof, including at least one recognition site capable of interacting with the sulfhydryl function of said glutathione GSH entity and/or of a said analog thereof, or
  molecularly imprinted polymer (MIP) comprising:
    one or more recognition sites for a glutathione GSH entity and/or for an analog thereof, and
    at least one residue of glutathione GSH or of a corresponding analogue thereof,
    said residue being trapped in the cavity of said molecularly imprinted polymer via an interaction of its native sulfhydryl function with one of said recognition sites.

* * * * *